(12) United States Patent
Frenzel et al.

(10) Patent No.: US 6,194,623 B1
(45) Date of Patent: Feb. 27, 2001

(54) HYDROGENATION OF ORGANIC COMPOUNDS WITH THE USE OF THE NEMCA EFFECT

(75) Inventors: Andrea Frenzel, Limburgerhof (DE); Constantinos G. Vayenas; Alexandros Giannikos, both of Patras (GR); Panagiotis Petrolekas, Athens; Constantinos Pliangos, Patras, both of (GR)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/371,848

(22) Filed: Aug. 11, 1999

(30) Foreign Application Priority Data

Aug. 21, 1998 (DE) .................................. 198 38 165

(51) Int. Cl.[7] .................................................. C07C 7/163
(52) U.S. Cl. .................... 585/259; 585/250; 585/260; 585/263
(58) Field of Search .................... 585/250, 259, 585/260, 263

(56) References Cited

U.S. PATENT DOCUMENTS 5,919,349  7/1999  Huber et al. ................... 205/413

FOREIGN PATENT DOCUMENTS 19620861  11/1997  (DE) .
0480 116  *  4/1992  (EP) .

OTHER PUBLICATIONS

Vayenas et al., "The Electrochemical Activation of Catalytic Reactions", *Modern Aspects of Electrochemistry*, 29, 1996, pp. 57–202.

* cited by examiner

*Primary Examiner*—Bekir L. Yildirim
(74) *Attorney, Agent, or Firm*—Keil & Weinkauf

(57) ABSTRACT

A process is provided for the selective hydrogenation of at least one organic compound having at least one unsaturated group, by bringing the at least one organic compound into contact with a hydrogen-containing gas in the presence of a catalyst, wherein the catalyst comprises an active material which is applied to a solid electrolyte to which, in turn, a metallic substrate is connected in such a way that a current flows through the solid electrolyte, so that the active material can be kept at a constant potential and a voltage is applied to

24 Claims, 2 Drawing Sheets

HYDROGENATION OF ORGANIC COMPOUNDS WITH THE USE OF THE NEMCA EFFECT

The present invention relates to a novel process for the selective hydrogenation of at least one organic compound which has at least one unsaturated group, use being made of the so-called NEMCA effect, and quite generally to the use of this effect for the selective hydrogenation of compounds of this type.

There are a wide range of processes for the hydrogenation of organic compounds. They are generally carried out with either homogeneous or heterogeneous catalysis which generally comprise metals, in particular metals in subgroup VIH of the Period Table, as active component.

Electrochemical hydrogenation of compounds of this type has in the past been carried out and described only very infrequently, at least one an industrial scale. An overview of reactions of this type and the relevant prior art is given by DE-A 196 20 861. According to that document, organic compounds are hydrogenated under the application of a voltage with a hydrogen-containing gas on a catalyst which is formed by in situ coating of the support material with the active metal.

The processes described in DE-A 196 20 861 use electrical equivalents in stoichiometric form as hydrogenation or reduction equivalents. In contrast to this, the NEMCA effect requires only catalytic quantities of electrical equivalents. It affects the selectivity of the catalytic hydrogenation.

The NEMCA effect per se has to date primarily been examined and described in the scientific literature. An overview of the reactions carried out to date is given in: "The Electrochemical Activation of Catalytic Reactions", C. G. Vayenas et al., Modern Aspects of Electrochemistry 29, J. Bockris et al., pub., Plenum Press, N.Y. 1996, pp. 57–202.

In consideration of the above prior art, one object of the present invention is to provide a novel process for the selective hydrogenation of organic compounds which have at least one unsaturated group, which in particular can be carried out in a way which is straightforward to implement, without the need for elaborate separation of the catalyst from the product which is obtained, and in which the hydrogenations of interest here can be carried out with high conversion ratio and at the same time high selectivity for the desired product.

This object is achieved by the method according to the invention.

Accordingly, the present invention relates to a process for the selective hydrogenation of at least one organic compound having at least one unsaturated group, by bringing the at least one organic compound into contact with a hydrogen-containing gas in the presence of a catalyst, characterized in that the catalyst comprises an active material which is applied to a solid electrolyte to which, in turn, a metallic substrate is connected in such a way that a current flows through the solid electrolyte, so that the active material can be kept at a constant potential and a voltage is applied to the catalyst during the hydrogenation.

As already indicated in the introduction, the so-called NEMCA effect (Non-Faradaic Electrochemical Modification of Catalytic Activity) is used in the implementation of the process according to the invention. This effect is based on the discovery that by applying an electric voltage between, on the one hand, an active material which is applied, preferably in the form of layers, to a solid electrolyte and, on the other hand, a further metallic substrate, likewise preferably in the form of layers, which is in turn connected to the solid electrolyte, it is possible for the activity or selectivity of a catalyst to be greatly altered.

In the scope of the present process, it is in principle possible to hydrogenate all organic compounds which have at least one selectively hydrogenatable unsaturated group.

Examples which may be mentioned in this regard include, amongst others, organic compounds which have two or more unsaturated groups of the same type, of which only a specific selection are hydrogenated in the scope of the novel process. Also envisagable are organic compounds which have at least two different unsaturated groups, of which one or more are selectively hydrogenated.

Naturally, a mixture of two or more organic compounds is also envisagable, each compound having at least one unsaturated group and each differing from the others in terms of at least one unsaturated group, it being possible for a specific selection of these organic compounds to be selectively hydrogenated in the process according to the invention.

Likewise, of course, mention may be made of mixtures of two or more different organic compounds which have the same unsaturated group, it being possible for a specific selection of these organic compounds to be selectively hydrogenated in the scope of the process according to the invention.

Preferably, unsaturated hydrocarbons, for example alkenes and/or alkynes, are selectively hydrogenated in the process according to the invention.

The present invention therefore relates in particular to a process, as described above, wherein the at least one organic compound having at least one unsaturated group is a hydrocarbon having C—C double bonding or at least one C—C triple bond, or a mixture of at least one hydrocarbon having at least one C—C double bond and at least one hydrocarbon having at least one C—C triple bond.

An example of this is, amongst others, the hydrogenation of dehydrolinalool to form linalool, in which the C—C triple bond is selectively hydrogenated. The product of this selective hydrogenation, linalool, is an important intermediate product for the production of perfumes and vitamins.

The present invention also relates to a process, as described above, wherein the at least one organic compound having at least one unsaturated group is ethyne or a mixture of ethene and ethyne.

In the scope of the present invention, it is thus for example possible, depending on the selected process conditions, when there is a mixture of ethene and ethyne, either to hydrogenate ethene selectively to form ethane, or to hydrogenate ethyne selectively to form ethene.

The catalyst used according to the invention consists of a composite which comprises at least one active material that is applied to a solid electrolyte which is in turn connected to a metallic substrate in such a way that a current flows through the solid electrolyte, so that the active material can be kept at a constant potential.

The active material used is preferably at least one catalytically active metal in subgroup VIE of the Period Table, alone or in combination with at least one further metal in subgroup I and/or VII. Among these, Pd, Pt, Ru, Rh, Au, Ag and Ni are preferably used as active material, and in particular preferably Pd, Pt and Rh. The catalytically active material is preferably applied in the form of a porous layer to a solid electrolyte, the layer generally having a thickness of from 0.001 to 1 mm, preferably from 0.001 to 0.050 mm.

An ion conducting and/or proton conducting solid electrolyte, preferably a ceramic material, is used according to the invention as the solid electrolyte. Examples of materials which can be used according to the invention as a solid electrolyte include: β"-Al$_2$O$_3$, β-Al$_2$O$_3$, Li$^+$, Na$^+$, K$^+$ conducting β-Al$_2$O$_3$, Nasicon (in this regard see "J. Electrochem. Soc., Vol. 145 No. 5, May 1998, p. 1518) and Nafion®, β"-Al$_2$O$_3$ being preferably used.

Suitable metallic substrates are likewise, in principle, all materials which can be used as a complementary electrode for the active material described above, including the metals of which the catalytic layer is made, use being in particular made of metals in subgroup I of the Period Table, and more preferably Au or Ag.

The level of the voltage applied during the hydrogenation (per electrochemical cell) is in the range of from +5 V to −5 V, preferably +2 V to −2 V and in particular +1 V to −1 V. The current produced by application of this voltage is in the range of from 0.1 to 100 $\mu$A/cm$^2$, its sign being defined by the direction of the voltage drop.

The hydrogenation is in general carried out at suitable pressures and temperatures, operation being in general carried out at temperatures in the range of from −200 to +200° C., preferably from room temperature to 100° C. and, in particular, from 500° C. to 100° C. at pressures in the range of from, in general, 0 to 50 bar, preferably 0 to 30 bar and, in particular, 0 to 10 bar. This being the case, operation may be carried out in the gas phase or in solution.

The hydrogenation gases used may be any gases which contain free hydrogen and do not have detrimental quantities of catalyst poisons, for example CO. For example, reformer off-gases may be used. Preferably, however, pure hydrogen is used as the hydrogenation gas. The process according to the invention for the hydrogenation of organic compounds may be carried out continuously or in batch mode, continuous operation being preferred.

The hydrogenation according to the invention may be carried out in the absence or presence of a solvent or diluent, that is to say it is not necessary to carry out the hydrogenation in solution.

Any suitable solvent or diluent may be used as the solvent or diluent. The choice is not in this case of critical importance, so long as the solvent or diluent used is capable of forming a homogeneous solution with the organic compound to be hydrogenated. For example, the solvent or diluent may also contain water.

Examples of a suitable solvent or diluent include the following:

Straight-chain or cyclic ethers, for example tetrahydrofuran or dixoane, and aliphatic alcohols in which the alkyl radical preferably has from 1 to 10 carbon atoms, in particular from 3 to 6 carbon atoms.

Examples of alcohols which may preferably be used include i-propanol, n-butanol, i-butanol and n-hexanol.

Aromatic solvents such as toluene or xylene may furthermore be used.

Mixtures of these or other solvents or diluents may likewise be used.

There is no particular restriction on the amount of solvent or diluent used, and this amount may be freely chosen as required, although preferred amounts are ones which lead to a solution with a strength of some 10 to 70% by weight of the organic compound intended for hydrogenation.

The molar ratio of hydrogen in the hydrogenation gas to the unsaturated groups in the organic compound to be hydrogenated may in general be freely chosen, and is preferably from 1 to 3.

The flow rates used in general when carrying out the process according to the invention, that is to say the throughput amount of gas mixture, which in general consists of the hydrogen-containing gas and the organic compound to be hydrogenated, is in general in the range of from 10 to 150 ml/min, preferably 15 to 50 ml/min, which corresponds to space-time velocities in the gas phase in the range of from $10^3$ to $1.5\times10^4$h$^{-1}$, or 0.1 to 1.5 h$^{-1}$ (in solution).

As can be seen from the above description, the present invention relates quite generally to the use of the NEMCA effect for the selective hydrogenation of at least one organic compound having at least one unsaturated group, in particular through the use of the NEMCA effect during the catalytic selective hydrogenation on the catalyst used for this.

The present invention will now be explained in terms of some examples with reference to two drawings, in which.

EXAMPLES

Example 1

Figure 1:
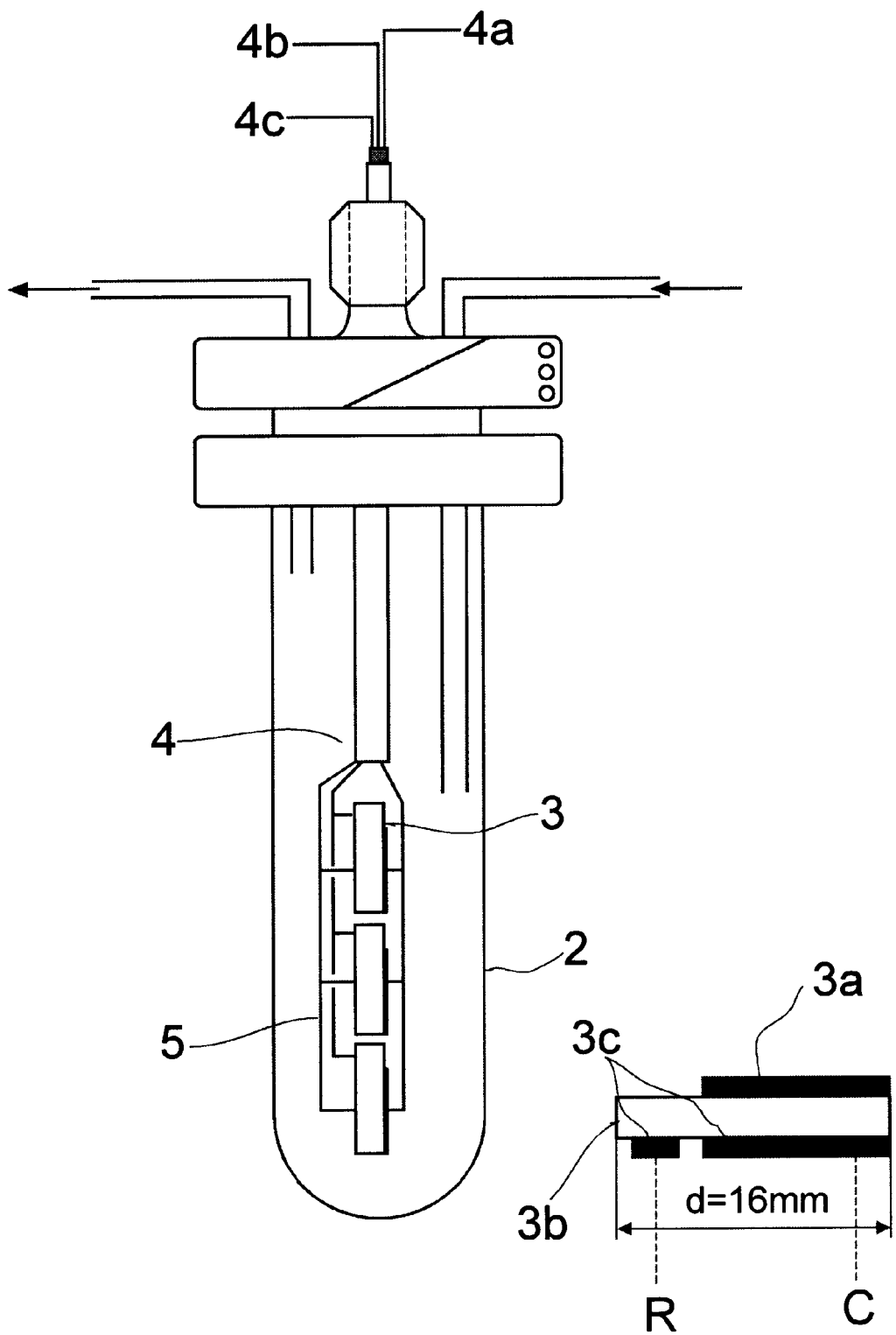
FIG. 1 shows the basic structure of the equipment used for carrying out the process according to the invention.

In Example 1, a mixture containing 1.3% by volume hydrogen, 0.7% by volume of acetylene and 7% by volume of ethylene was introduced through the inlet (1) into the equipment shown in FIG. 1. This equipment consisted of a quartz tube (2), into which the catalyst (3), held by a ceramic holder (4), was introduced. As shown by the accompanying detailed drawing of the catalyst (3), the active material which this catalyst comprised was a thin layer (3a) of Pd as the working electrode. The layer thickness of the active material was about 10 $\mu$m. This layer of active material was applied to a β"-Al$_2$O$_3$ solid electrolyte (3b) which, on its opposite side, was provided in turn with a metallic substrate (3c) consisting of two layers of Au as reference electrode [R] and complementary electrode [C], respectively. The thickness of this layer was about 10 $\mu$m.

In order to increase the catalytically active area, the catalyst used here consisted of three composites (pellets) as described above, connected one after the other, by means of which the active catalyst area was increased.

In this device, a voltage of +0.5 V relative to the reference electrode (3c) was applied to the catalyst layer (3a). The relevant electrode configuration, also shown in FIG. 1, consisted of a working electrode (4a), a reference electrode (4b) and a complementary electrode (4c), the potential being applied to the catalyst via gold wires (5).

The hydrogenation was carried out at 70° C. and 1 atm total pressure.

Figure 2:
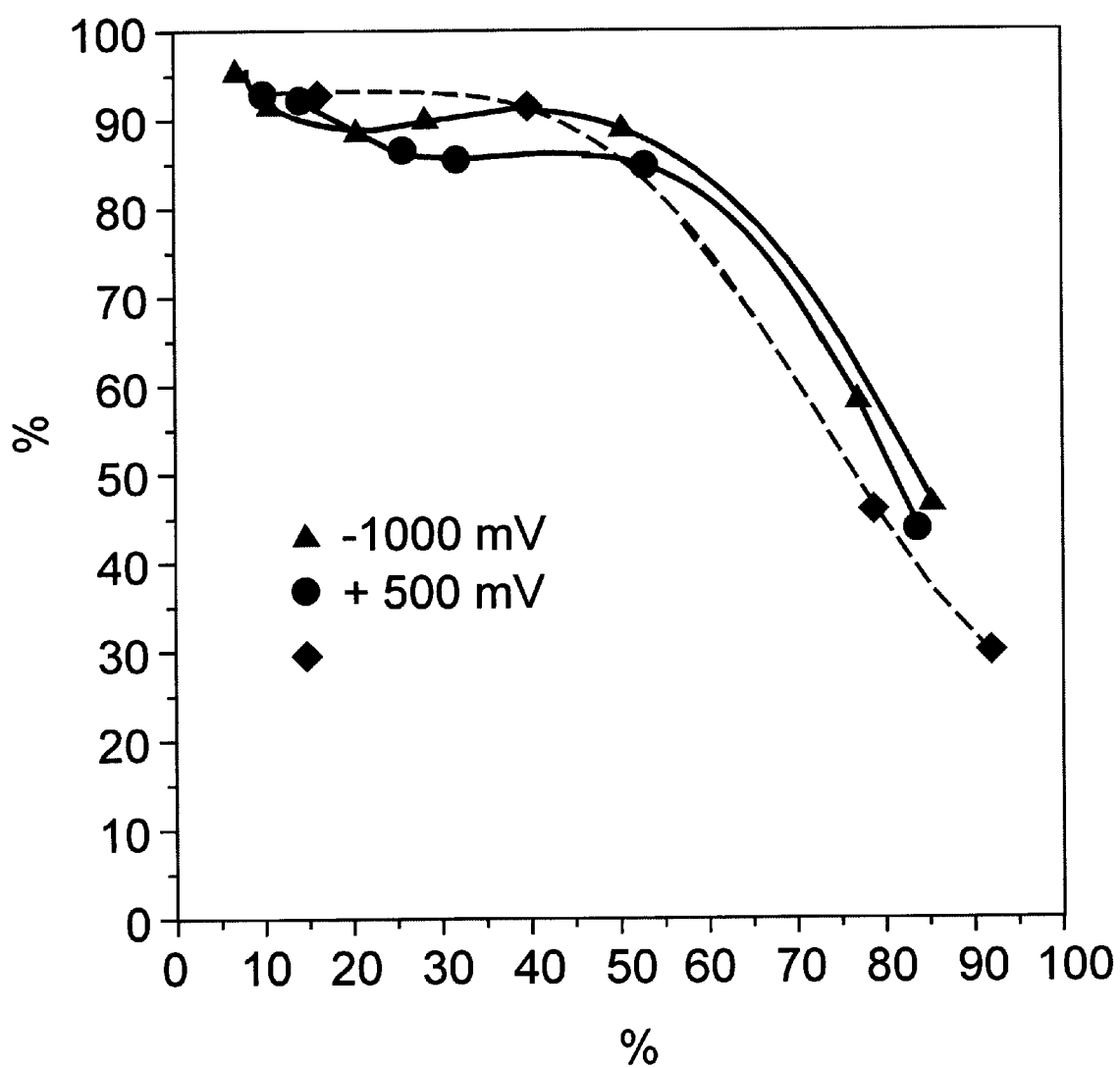
FIG. 2 shows the results of the reactions described below according to Examples 1 and 2, in comparison with a corresponding reaction using standard catalysts, for example Pd on SiO$_2$ or Pd/Ag on β-Al$_2$O$_3$. The conversion ratio in % is plotted on the abscissa in FIG. 2, and the selectivity in % is plotted on the ordinate.

The results of this example are reported in FIG. 2 (dark circles ●).

Example 2

Example 2 was carried out in similar fashion to Example 1, but with the voltage applied to the catalyst being −1 V relative to the complementary electrode. The results are represented in FIG. 2 in the form of black triangles.

The results of Examples 1 and 2 are graphically represented in FIG. 2. For comparison, the results of a corresponding reaction using a conventional supported catalyst have also been shown in FIG. 2 (◆).

They may be summarized as follows:

The selectivity of the system according to Example 1 is, up to conversion ratios of 50%, less than when a conventional supported catalyst is used. Above a conversion ratio of 70%, the selectivity of the system is, however, somewhat higher. Compared with Example 2, the performance of the system according to this example is somewhat worse.

It is only up to conversion ratios of 40% that the system according to Example 2 has worse performance than when a conventional supported catalyst is used. For conversion ratios in excess of 40%, this system works considerably better than when a conventional supported catalyst is used. It is overall also better than the system according to Example 1.

What is claimed is:

1. A process for the selective hydrogenation of at least one organic compound having at least one unsaturated group, by bringing the at least one organic compound into contact with a hydrogen-containing gas in the presence of a catalyst, wherein the catalyst comprises an active material which is applied to a solid electrolyte to which, in turn, a metallic substrate is connected in such a way that a current flows through the solid electrolyte, so that the active material can be kept at a constant potential and a voltage is applied to the catalyst during the hydrogenation.

2. A process for the selective hydrogenation of at least one organic compound having at least one unsaturated group, by bringing the at least one organic compound into contact with a hydrogen-containing gas in the presence of a catalyst, wherein the catalyst comprises an active material which is applied to a solid electrolyte to which, in turn, a metallic substrate is connected in such a way that a current flows through the solid electrolyte, so that the active material can be kept at a constant potential and a voltage is applied to the catalyst system during the hydrogenation, and wherein the at least one unsaturated group of the at least one organic compound is at least one C—C double bond or at least one C—C triple bond.

3. The process of claim 1, wherein the at least one organic compound having at least one unsaturated group is ethyne or a mixture of ethene and ethyne.

4. The process of claim 1, wherein the active material is a metal in subgroup VIII of the Periodic Table, alone or in combination with at least one metal selected from subgroups I and VII of the Periodic Table.

5. The process of claim 1, wherein the solid electrolyte is a ceramic which is protonically conducting or ionically conducting, or which is both protonically conducting and ionically conducting.

6. The process of claim 5, wherein the ceramic is selected from the group consisting of $\beta''\text{-}Al_2O_3$, $\beta\text{-}Al_2O_3$, $Li^+$, $Na^+$, $K^+$ conducting $\beta\text{-}Al_2O_3$, and Nasicon.

7. The process of claim 1, which is carried out at a temperature in the range of from $-200°$ C. to $+200°$ C. and a pressure of from 0 to 50 bar.

8. The process of claim 1, wherein the voltage applied to the catalyst system is in the range of from +5 V to −5 V per electrochemical cell.

9. The method of applying the NEMCA effect to the catalytic hydrogenation of at least one organic compound having at least one unsaturated group, wherein the catalytic hydrogenation on the catalyst is a catalytic selective hydrogenation.

10. The process of claim 2, wherein the at least one organic compound is a mixture of at least one hydrocarbon having at least one C—C double bond and at least one hydrocarbon having at least one C—C triple bond.

11. The process of claim 2, wherein the at least one organic compound having at least one unsaturated group is ethyne or a mixture of ethene and ethyne.

12. The process of claim 2, wherein the active material is a metal in subgroup VIII of the Periodic Table, alone or in combination with at least one metal selected from subgroups I and VII of the Periodic Table.

13. The process of claim 2, wherein the solid electrolyte is a ceramic which is protonically conducting or ionically conducting, or which is both protonically conducting and ionically conducting.

14. The process of claim 13, wherein the ceramic is selected from the group consisting of $\beta''\text{-}Al_2O_3$, $\beta\text{-}Al_2O_3$, $Li^+$, $Na^+$, $K^+$ conducting $\beta\text{-}Al_2O_3$, and Nasicon.

15. The process of claim 2, which is carried out at a temperature in the range of from $-200°$ C. to $+200°$ C. and a pressure of from 0 to 50 bar.

16. The process of claim 2, wherein the voltage applied to the catalyst system is in the range of from +5 V to −5 V per electrochemical cell.

17. A process for the selective catalytic hydrogenation of at least one unsaturated hydrocarbon compound, by bringing the at least one unsaturated hydrocarbon compound into contact with a hydrogen-containing gas in the presence of a catalyst, wherein the catalyst comprises an active material which is applied to a solid electrolyte to which, in turn, a metallic substrate is connected in such a way that a current flows through the solid electrolyte, so that the active material can be kept at a constant potential and a voltage is applied to the catalyst system during the hydrogenation.

18. The process of claim 17, wherein the hydrocarbon compound has at least one unsaturated group selected from a C—C double bond and a C—C triple bond.

19. The process of claim 18, wherein the unsaturated hydrocarbon compound is an alkene or an alkyne.

20. The process of claim 17, wherein the active material is a metal in subgroup VIII of the Periodic Table, alone or in combination with at least one metal selected from subgroups I and VII of the Periodic Table.

21. The process of claim 17, wherein the solid electrolyte is a ceramic which is protonically conducting or ionically conducting, or which is both protonically conducting and ionically conducting.

22. The process of claim 21, wherein the ceramic is selected from the group consisting of $\beta''\text{-}Al_2O_3$, $\beta\text{-}Al_2O_3$, $Li^+$, $Na^+$, $K^+$ conducting $\beta\text{-}Al_2O_3$, and Nasicon.

23. The process of claim 17, which is carried out at a temperature in the range of from $-200°$ C. to $+200°$ C. and a pressure of from 0 to 50 bar.

24. The process of claim 17, wherein the voltage applied to the catalyst system is in the range of from +5 V to −5 V per electrochemical cell.

* * * * *

UNITED STATES PATENT AND TRADEMARK OFFICE
CERTIFICATE OF CORRECTION

PATENT NO. : 6,194,623 B1
DATED : February 27, 2001
INVENTOR(S) : Frenzel et al.

It is certified that error appears in the above-identified patent and that said Letters Patent is hereby corrected as shown below:

Column 5, claim 5,
Line 47, "tonically" should be -- ionically --.

Column 6, claim 21,
Line 50, "tonically" should be -- ionically --.

Signed and Sealed this

Sixth Day of November, 2001

*Attest:*

NICHOLAS P. GODICI
*Attesting Officer*    *Acting Director of the United States Patent and Trademark Office*